United States Patent [19]

Beck et al.

[11] Patent Number: 4,960,899
[45] Date of Patent: Oct. 2, 1990

[54] N-SULPHENYLATED 2-AMINO-4-CHLORO-THIAZOLE-SULPHONAMIDES, THEIR USE, PROCESS FOR THEIR PREPARATION, AND THE INTERMEDIATES 2,4-DICHLOROTHIAZOLE-SULPHONYL CHLORIDE AND 2-AMINO-4-CHLORO-THIAZOLE-SULPHONAMIDES

[75] Inventors: Gunther Beck; Bernd Baasner, both of Leverkusen; Michael Schwamborn, Koeln; Wilheim Brandes, Leichlingen, all of Fed. Rep. of Germany

[73] Assignee: Bayer Aktiengesellschaft, Leverkusen, Fed. Rep. of Germany

[21] Appl. No.: 487,679

[22] Filed: Mar. 2, 1990

Related U.S. Application Data

[62] Division of Ser. No. 308,180, Feb. 8, 1989, Pat. No. 4,906,650.

[30] Foreign Application Priority Data

Feb. 18, 1988 [DE] Fed. Rep. of Germany ....... 3805058

[51] Int. Cl.⁵ .......................................... C07D 277/36
[52] U.S. Cl. .................................... 598/186
[58] Field of Search .......................... 548/186

[56] References Cited

FOREIGN PATENT DOCUMENTS 328999 8/1989 European Pat. Off. ............ 548/188

*Primary Examiner*—Robert Gerstl
*Attorney, Agent, or Firm*—Sprung, Horn, Kramer & Woods

[57] ABSTRACT

The fungicidally active N-sulphenylated 2-amino-4-chloro-thiazole-sulphonamides of the formula

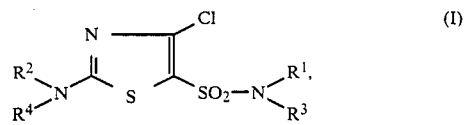

wherein $R^1$ and $R^2$ independently of one another denote hydrogen, alkyl, alkenyl, alkinyl, cycloalkyl, aryl, aralkyl or an aromatic or a non-aromatic heterocyclic radical and $R^3$ and $R^4$ independently of one another stand for hydrogen, alkyl, cycloalkyl, aryl or aralkyl or for the dichlorohalogenomethyl-sulphenyl radical —S—$CCl_2$X, in which X denotes fluorine, chlorine or bromine, and where furthermore one of the pairs of substitutents $R^1$ and $R^3$ or $R^2$ and $R^4$ together with the nitrogen atom which they substitute can denote morpholino or thiomorpholino, with at least one of the radicals $R^3$ and $R^4$ standing for the radical —S—$CCl_2$X, can be prepared in a process in which, in a first step, 2,4-dichloro-thiazole is reacted with chlorosulphonic acid to give 2,4-dichloro-thiazole-sulphonyl chloride, in which, in a second step, the 2,4-dichloro-thiazole-sulphonyl chloride is reacted with primary amines or with a primary and a secondary amine to give 2-amino-4-chloro-thiazolesulphonamides, and in which, in a third step, the sulphonamides mentioned are reacted with dichlorohalogenomethylsulphenyl chlorides to give the substances of the formula (I).

1 Claim, No Drawings

N-SULPHENYLATED 2-AMINO-4-CHLORO-THIAZOLE-SULPHONA-MIDES, THEIR USE, PROCESS FOR THEIR PREPARATION, AND THE INTERMEDIATES 2,4-DICHLOROTHIAZOLE-SULPHONYL CHLORIDE AND 2-AMINO-4-CHLORO-THIAZOLE-SULPHONA-MIDES

This is a division, of application Ser. No. 308,180, filed Feb. 8, 1989, now U.S. Pat. No. 4906650.

BACKGROUND OF THE INVENTION

The present invention relates to the new N-sulphenylated 2-amino-4-chloro-thiazole-sulphonamides, a process for their preparation, their use as plant protection agents, and the intermediates occurring during the preparation.

It has been known for a long time that N-trihalogenomethylthio compounds can be used as fungicides in agriculture and horticulture. Thus, for example, N-(trichloromethylthio)-tetrahydrophthalimide (German Pat. Specification 887,506) and N,N-dimethyl-N'-phenyl-N'-(dichlorofluoromethylthio)-sulphonamide (German Pat. Specification 1,193,498) are employed in fruit growing and viticulture for combating fungal diseases. Furthermore, N-(dichlorofluoromethylthio)-benzenesulphonamides, such as, for example, N-dichlorofluoromethylthio-N-methyl-3,4-dichlorobenzene- or 3-nitrobenzene-sulphonamide, are also known (see also German Pat. Specification 1,193,498).

SUMMARY OF THE INVENTION

The new N-sulphenylated 2-amino-4-chloro-thiazolesulphonamides of the formula

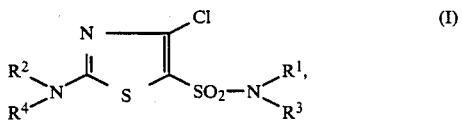

(I)

wherein
R$^1$ and R$^2$ independently of one another denote hydrogen, alkyl, alkenyl, alkinyl, cycloalkyl, aryl, aralkyl, or an aromatic or non-aromatic heterocyclic radical and R$^3$ and R$^4$ independently of one another stand for hydrogen, alkyl, cycloalkyl, aryl or aralkyl, or for the dichlorchalogenomethyl-sulphenyl radical —S—CCl$_2$X, in which X denotes fluorine, chlorine or bromine,
with at least one of the radicals R$^3$ and R$^4$ standing for the radical —S—CCl$_2$X, have been found.

Furthermore, a process for the preparation of the substances of the formula (I) has been found, which is characterized in that, in a first step, 2,4-dichlorothiazole is reacted with chlorosulphonic acid to give 2,4-dichloro-thiazole-sulphonyl chloride of the formula

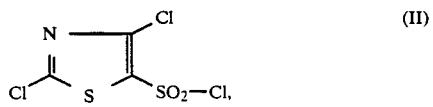

(II)

in a second step, the 2,4-dichloro-thiazole-sulphonyl chloride (II) is reacted with amines of the formulae

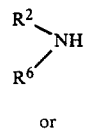

(III)

or

(IV)

in which
R$^1$ and R$^2$ have the abovementioned meaning and R$^5$ and R$^6$ independently of one another stand for hydrogen, alkyl, cycloalkyl, aryl or aralkyl,
with at least one of the radicals R$^5$ and R$^6$ denoting hydrogen, to give 2-amino-4-chloro-thiazole-sulphonamides of the formula

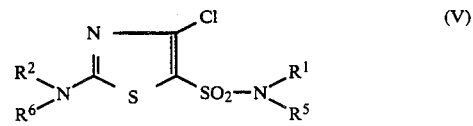

(V)

wherein
R$^1$, R$^2$, R$^5$ and R$^6$ have the abovementioned meaning and, in a third step, the 2-amino-4-chloro-thiazolele sulphonamides (V) are reacted with di-chlorohalogenomethyl-sulphenyl chlorides of the formula

Cl—S—CCl$_2$X (VI)

wherein
X denotes fluorine, chlorine or bromine to give the substances of the formula (I).

The invention furthermore relates to the new intermediates of the formulae (II) and (V).

DETAILED DESCRIPTION OF THE INVENTION

Alkyl denotes straight-chain or branched C$_1$–C$_8$alkyl, preferably C$_1$–C$_6$-alkyl, particularly preferably C$_1$–C$_5$-alkyl, such as methyl, ethyl, propyl, isopropyl, butyl, isobutyl, tert.-butyl, straight-chain or branched pentyl, hexyl, heptyl or octyl.

Alkenyl denotes straight-chain or branched C$_3$–C$_8$alkenyl which is derived from the alkyl mentioned by replacing a single bond by a double bond; C$_3$–C$_6$-alkenyl is preferred, C$_3$–C$_5$-alkenyl is particularly preferred. Examples are: allyl, crotyl, pentenyl, hexenyl and octenyl. A preferred alkenyl is allyl or crotyl.

Alkinyl denotes C$_3$–C$_8$-alkinyl which is derived from the alkyl mentioned by replacing a single bond by a triple bond; C$_3$–C$_6$-alkinyl is preferred, C$_3$–C$_5$-alkinyl is particularly preferred. Examples are: propargyl, butinyl, pentinyl and octinyl. The preferred alkinyl is propargyl.

Cycloalkyl denotes C$_3$–C$_8$-cycloalkyl, preferably C$_3$–C$_7$-cycloalkyl, particularly preferably C$_3$–C$_6$-cycloalkyl. Examples which may be mentioned are: cyclopropyl, cyclobutyl, cyclopentyl, cyclohexyl, cycloheptyl or cyclooctyl.

Aryl has 6–12 carbon atoms and denotes, for example, phenyl, 1-naphthyl, 2-naphthyl or diphenyl; phenyl is preferred.

Aralkyl has 7-12 carbon atoms and denotes, for example, benzyl, phenyl-ethyl, naphthyl-methyl or naphthylethyl; benzyl and phenylethyl are preferred.

Aromatic or non-aromatic heterocyclic radicals denote 5- or 6-membered rings in which one or more carbon atoms are replaced by N, O and/or S atoms, such as 2-furyl, 2-thienyl, 2-tetrahydrofuryl, 2-pyranyl, 5-pyrrolyl, 2imidazolyl, 3-(1,2,4-triazolyl), 2-, 3- or 4-pyridyl, 2- or 4-pyrimidyl, 2-pyrrolidyl, 2-piperidyl, 2-morpholinyl and 2-thiomorpholinyll Preferred heterocyclic radicals are 2-furyl, 2-, 3- or 4-pyridyl, 2- or 4-pyrimidyl and 2-morpholinyl.

The alkyl radicals, alkenyl radicals, alkinyl radicals, cycloalkyl radicals, aryl radicals, aralkyl radicals or the aromatic or non-aromatic heterocyclic radicals mentioned can be monosubstituted or polysubstituted by $C_1$-$C_4$-alkyl of the type mentioned, preferably methyl or ethyl, by halogen, such as fluorine, chlorine or bromine, preferably fluorine or chlorine, or $C_1$-$C_4$alkoxy, such as methoxy, ethoxy, propoxy, isopropoxy, butoxy, isobutoxy, tert.-butoxy, preferably methoxy or ethoxy, or $C_1$-$C_4$-alkylthio, such as methylthio, ethylthio, propylthio, isopropylthio, butylthio, isobutylthio or tert.-butylthio, preferably methylthio.

All the substances of the formula (I) according to the invention are characterized by at least one dichlorohalogenomethylthio group on the nitrogen in connection with the 2-amino-4-chloro-5-sulphonamidothiazole structure. The formula (I) thus encompasses the following subgroups:

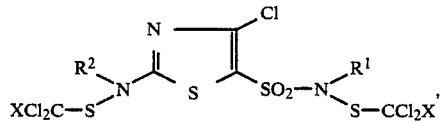

(Ia)

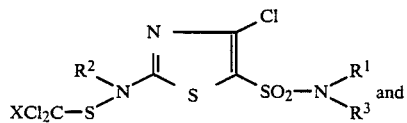

(Ib)

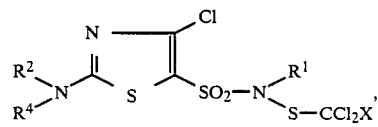

(Ic)

wherein
$R^1$, $R^2$, $R^3$, $R^4$ and X have the abovementioned meaning.

Preferred N-sulphenylated 2-amino-4-chloro-thiazole-sulphonamides are those of the formula

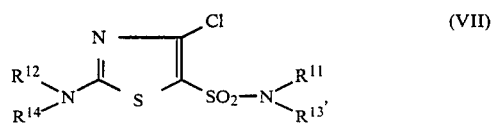

(VII)

in which
$R^{11}$ and $R^{12}$ independently of one another denote straight-chain or branched C1-C6-alkyl, allyl, crotyl, propargyl, $C_3$–$C_6$-cycloalkyl, phenyl, benzyl, phenylethyl, 2-furyl, 2-, 3- or 4-pyridyl, 2- or 4-pyrimidyl or 2-morpholinyl and $R^{13}$ and $R^{14}$ independently of one another stand for hydrogen, straight-chain or branched $C_1$–$C_6$-alkyl, $C_3$–$C_6$-cycloalkyl, phenyl, benzyl or phenylethyl or for the dichlorohalogenomethylsulphenyl radical —S—$CCl_2$X in which X denotes fluorine, chlorine or bromine,
with at least one of the radicals $R^{13}$ and $R^4$ standing for the radical —S—$CCl_2$X.

Particularly preferred N-sulphenylated 2-amino-4-chloro-thiazole-sulphonamides are those of the formula

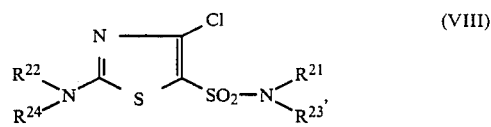

(VIII)

in which
$R^{21}$ and $R^{22}$ independently of one another denote straight-chain or branched $C^1$-$C^6$-alkyl, allyl, crotyl, propargyl, $C_3$-$C_6$-cycloalkyl, phenyl or benzyl and
$R^{23}$ and $R^{24}$ independently of one another stand for hydrogen, straight-chain or branched $C_1$-$C_6$-alkyl or the dichlorohalogenomethylsulphenyl radical —S—$CCl_2$X in which X denotes fluorine, chlorine or bromine,
with at least one of the radicals $R^{23}$ and $R^{24}$ standing for the radical —S—$CCl_2$X.

Amines (III) or (IV) and substances (V) having the corresponding range of meanings are employed for their preparation.

Besides the compounds of the formula (I) mentioned in the Use Examples, additional reference may also be made to the following individual compounds:

| No. | $R^1$ | $R^3$ | $R^2$ | $R^4$ |
|---|---|---|---|---|
| Ia.1 | $CH_3$ | $SCFCl_2$ | $CH_3$ | $SCFCl_2$ |
| Ic.1 | $CH_3$ | $SCFCl_2$ | $CH_3$ | $CH_3$ |
| Ic.2 | $CH_3$\\$CH$/$CH_3$ | $SCFCl_2$ | $CH_3$ | $CH_3$ |
| Ib.1 | $CH_3$ | $CH_3$ | $CH_3$\\$CH$/$CH_3$ | $SCFCl_2$ |
| Ib.2 | $CH_3$ | $CH_3$ | $C_6H_5$ | $SCFCl_2$ |
| Ia.2 | $C_2H_5$ | $SCFCl_2$ | $C_2H_5$ | $SCFCl_2$ |

-continued

| No. | R¹ | R³ | R² | R⁴ |
|---|---|---|---|---|
| Ib.3 | CH₃ | CH₃ | CH₃ | SCFCl₂ |
| Ia.3 | (CF₃)(CH₃)CH— | SCFCl₂ | (CF₃)(CH₃)CH— | SCFCl₂ |
| Ia.4 | CH₃—O—(CH₂)₃— | SCFCl₂ | CH₃O—(CH₂)₃— | SCFCl₂ |
| Ia.5 | CH₃ | SCFCl₂ | (CH₃)₂CH— | SCFCl₂ |
| Ia.6 | (CH₃)₂CH— | SCFCl₂ | CH₃ | SCFCl₂ |
| Ib.4 | (CF₃)(CH₃)CH— | H | (CF₃)(CH₃)CH— | SCFCl₂ |
| Ic.3 | CH₃ | SCFCl₂ | C₆H₅ | H |
| Ia.7 | (CH₃)₃C—CH₂— | SCFCl₂ | (CH₃)₃C—CH₂— | SCFCl₂ |
| Ib.5 | Cyclopropyl | SCFCl₂ | Cyclopropyl | SCFCl₂ |
| Ic.4 | Cyclopropyl | SCFCl₂ | CH₃ | CH₃ |
| Ic.5 | CH₂=CH—CH₂ | SCFCl₂ | CH₃ | CH₃ |
| Ic.6 | CH≡C—CH₂ | SCFCl₂ | CH₃ | CH₃ |

In order to prepare &he substances according to formula (I), 2,4-dichloro-thiazole is reacted, in a fir$t step, with 2-20 moles, preferably 5-15 moles, of chlorosulphonic acid at a temperature near the boiling point of the reaction mixture. The excess chlorosulphonic acid simultaneously serves as the solvent.

In a second step of the process for the preparation of substances of the formula (I), 2,4-dichloro-thiazolesulphonyl chloride is reacted with amines of the formulae (III) and/or (IV) to give 2-amino-4-chloro-thiazole-sulphonamides of the formula (V).

This reaction is carried out with primary amines or a primary and a secondary amine, so that in the resulting substance of the formula (V) at least one H atom remains on the nitrogen. It has been found that the sulphonyl chloride group reacts before the chlorine atom in the 2-position, while the chlorine atom in the 4-position does not react under the conditions according to the invention. The second step of the process according to the invention can therefore be carried out in a plurality of variants, which permits the preparation of a large variety of substances of formulae (V) and (I):

In a first variant, the sulphonyl chloride is initially reacted with a primary amine and then with a secondary amine, resulting in an H atom on the nitrogen in the sulphonamide group.

In a second variant, the sulphonyl chloride is initially reacted with a secondary amine and then with a primary amine, resulting in an H atom on the nitrogen in the amino group in the 2-position.

In a third variant, the sulphonyl chloride is initially reacted with a first primary amine and then with a second primary amine, in which process one H atom is positioned on each N atom and in which process furthermore the two N atoms can be provided with various organic substituents.

Finally, in a fourth variant, both the sulphonyl chloride group and the Cl atom in the 2-position are reacted by the same primary amine, in which process again one H atom is positioned on the two N atoms, the two N atoms being provided with the same substituent.

1-1.5 moles, preferably 1-1.1 moles, particularly preferably 1-1.05 moles, of an amine of the formulae (III) or (VI) is employed per mole of Cl atom to be reacted in the 2,4-dichlorothiazolesulphonyl chloride. The temperature for the reaction of the sulphonyl chloride group is lower than the temperature for the reaction of the Cl atom in the 2-position However, when the process is carried out carefully, the temperature for the reaction of the sulphonyl chloride group can slightly extend into the range for the reaction of the Cl atom in the 2-position. In this context, carefully carrying out the procedure is taken to mean, for example, the slow, dropwise addition of the amine chosen for the reaction with the sulphonyl chloride group, avoiding an, or tolerating only a small, excess of amine, or diluting the substance (II) to a relatively large extent. The lower temperature range is for example −80° C. to +20° C., preferably −60° C. to 0° C., particularly preferably −40° C. to −20° C. The higher temperature range is generally 0°-100° C., preferably 0°-50° C. In the event that the sulphonyl chloride group and the Cl atom in the 2-position are reacted with the same primary amine, there is no need to employ the lower temperature; the reaction is immediately carried out in the higher temperature range In the event that in the lower temperature range small amounts (up to approx 5 %) of chlorine in the 2-position react even when the reaction is carried out carefully, such an undesired reaction product can be separated off after previous identification, for example by thin-layer chromatography by suitable purification methods, for example fractional crystallization or a suitable chromatographic method The various variants of the second step of the process according to the invention are carried out in the presence of a base as the acid-binding agent and if appropriate in the presence of a diluent A suitable diluent can be important, for example, for bringing the mixture to the desired temperature in the low temperature range while simultaneously maintaining the liquid phase.

Acid-binding agents which can be used are inorganic bases, such as sodium hydroxide, sodium carbonate and others, or tertiary amines, such as pyridine, triethylamine or others. These types of acid-binding agents are known to those skilled in the art. The acid-binding agents are employed in an equimolar amount relative to the primary or secondary amines employed. However, the amine to be reacted itself can be employed as the acid-binding agent, which is then employed in twice the molar amount relative to the Cl atom to be reacted as indicated above. This variant is particularly suitable for the reaction of the Cl atom in the 2-position or in the reaction of the sulphonyl chloride group and the Cl atom in the 2-position with the same primary amine.

Suitable diluents are all solvents which are inert with respect to the reaction. These include, for example, hydrocarbons, such as toluene, hexane, cyclohexane and others, halogenohydrocarbons, such as methylene chloride, chlorobenzene and others, and ethers, such as dioxane, tetrahydrofuran, diethyl ether and others, and also water. When water is also used, it is possible to work in the homogeneous phase and in the heterogeneous phase. Partial freezing of water was not observed, even at low temperatures, and, besides, would not interfere with the process according to the invention For example, 0.1–15 1, preferably 0.2–6 1, of diluent are employed per mole of substance (II) to be reacted, but this amount is not crucial. Economical and ecological factors suggest the employment of the lowest possible amount of diluent; such amounts can be determined by simple preliminary experiments From the 2-amino-4-chloro-thiazole-sulphonamides of the formula (V) resulting from the second step of the process according to the invention, reference may be made by way of example, besides the Use Examples, to the following substances which are characterized by their substituents:

| No. | $R^1$ | $R^5$ | $R^2$ | $R^6$ |
|---|---|---|---|---|
| V.1 | $CH_3$ | H | $CH_3$ | H |
| V.2 | $CH_3$ | H | $CH_3$ | $CH_3$ |
| V.3 | $CH_3$ | $CH_3$ | $CH_3$ | H |
| V.4 | $CH_3$ | $CH_3$ | $(CH_3)_2CH-$ | H |
| V.5 | $CH_3$ | $CH_3$ | $C_6H_5$ | H |
| V.6 | $C_2H_5$ | H | $C_2H_5$ | H |
| V.7 | $(CH_3)_3C-CH_2-$ | H | $(CH_3)_3C-CH_2-$ | H |
| V.8 | $(CF_3)(CH_3)CH-$ | H | $(CF_3)(CH_3)CH-$ | H |
| V.9 | $CH_3O-(CH_2)_3$ | H | $C_6H_5$ | H |
| V.10 | $CH_3$ | H | $(CH_3)_2CH-$ | H |
| V.11 | $(CH_3)_2CH-$ | H | $CH_3$ | H |
| V.12 | $CH_3$ | H | $C_6H_5$ | H |
| V.13 | Cyclopropyl | H | Cyclopropyl | H |
| V.14 | Cyclopropyl | H | $CH_3$ | $CH_3$ |
| V.15 | $CH_2=CH-CH_2$ | H | $CH_3$ | $CH_3$ |
| V.16 | $CH\equiv C-CH_2$ | H | $CH_3$ | $CH_3$ |

In the third step of the process according to the invention, 2-amino-4-chloro-thiazole-sulphonamides of the formula (V) are reacted with the abovementioned dichlorohalogenomethylsulphenyl chloride of the formula (VI) to give the end product of the formula (I). The halogen X in the dichlorohalogenomethyl group is fluorine, chlorine or bromine, preferably fluorine or chlorine, particularly preferably fluorine Such dichlorohalogenomethyl-sulphenyl chlorides are known to those skilled in the art (Angew. Chem. 76 (1964), 807).

The dichlorohalogenomethyl-sulphenyl chloride is employed in an amount of 0.9–1.2, preferably 0.95–1.1, particularly preferably 1–1.05, moles per equivalent of H atoms to be reacted.

This reaction is carried out at temperatures in the range 0°–100° C., preferably 20°≦50° C., in the presence of acid-binding agents of the type mentioned above in the second process step Suitable diluents for the third step of the process according to the invention are the solvents which have already been mentioned above in the second step, in the indicated amounts For example, this third step is carried out as described below: a compound of the formula (V) and a sulphenyl chloride of the formula (VI) in the amount mentioned are initially introduced into one of the diluents mentioned, for example at room temperature The acid-binding agent is then added in portions, so that the reaction temperature which increases during this process remains within the indicated range. When the reaction is complete, the N-sulphenylated 2-amino-4-chloro-thiazole-sulphonamide is precipitated using water and isolated in a known manner (for example by filtration or centrifuging) and purified (for example by recrystallization or a chromatographic method)

If 2 moles of sulphenyl chloride (VI) per mole of the substance (V) are employed, and in the event that (V) carries hydrogen in the sulphonamide group and in the amino group, N-sulphenylated 2-amino-4-chloro-thiazolesulphonamides of the subgroup (Ia) are obtained. If amounts of (VI) of less than 2 moles per mole of (V) are employed, mixtures of (Ia), (Ib) and (Ic) are obtained; also, if approximately 1 mole of (VI) is employed per mole of (V), mixtures of (Ib) and (Ic) are obtained, occasionally with small proportions of (Ia). Such mixtures can be separated, for example by crystallization or chromatography, often more favourably by chromatography. If parts of the separated mixture are not to be used, they can be subjected to acid hydrolysis (for example using HCl or $H_2SO_4$ of various concentrations); in this process, the $-S-CCl_2X$ group is split off and the remaining substance (V) is available as a valuable intermediate for the third step of the process according to the invention.

In many cases, the sulphonamide group in (V) is more reactive than the amino group, so that subgroup (Ic), in which the amino group carries hydrogen, is unambiguously formed.

In the cases where the sulphonamide group is deactivated by $R^1$ or $R^3$, the reaction occurs mainly on the amino group, with hydrogen remaining the sulphonamide group.

The N-sulphenylated 2-amino-4-chloro-thiazolesulphonamide of the formula (I) exhibit a good fungicidal activity in plant protection, combined with good tolerance by plants. Surprisingly, this fungicidal activity is higher than that of the compounds known from the prior art, which are structurally very similar and have a very similar type of action. Their particular activity is aimed at the causative organism of apple scab and against grey mould.

The good toleration by plants of the active compounds at the concentrations required for combating plant diseases, permits treatment of above-ground parts of plants, of vegetative propagation stock and seeds, and the treatment of the soil.

The active compounds can be converted to the customary formulations, such as solutions, emulsions, suspensions, powders, foams, pastes, granules, aerosals, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and-/or dispersing agents, and/or foam-forming agents In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as lower halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is furthermore possible to use colorants such as inorganic pigments, for example iron oxide, titanium oxide and Prussian Blue, and organic dyestuffs, such as alizarin dyestuffs, azo dyestuffs and metal phthalocyanine dyestuffs, and furthermore trace nutrients such as salts of iron, manganese, boron, copper, cobalt, molybdenum and zinc.

The formulations in general contain between 0.1 and 95 per cent by weight of active compound, preferably between 0.5 and 90%. The active compounds according to the invention can be present in the formulations as a mixture with other known active compounds, such as fungicides, insecticides, acaricides and herbicides, as well as in mixtures with fertilizers and growth regulators.

The active compounds can be u$ed as such or in the form of their formulations or the u$e forms prepared therefrom, such as ready-to-use solutions, emulsifiable concentrates, emulsions, foams, suspensions, wettable powders, pastes, soluble powders, dusts and/or granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plant$, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

In the treatment of soil, active compound concentrations of 0 00001 to 0.1% by weight, preferably 0.0001 to 0.02% by weight, are required at the place of action.

The invention thus furthermore relates to the use of the N-sulphenylated 2-amino-4-chloro-thiazole-sulphonamides of the formula (I) in plant protection, preferably as fungicides.

PREPARATION EXAMPLES

Example 1

Preparation of 2,4-dichlorothiazole-sulphonyl chloride

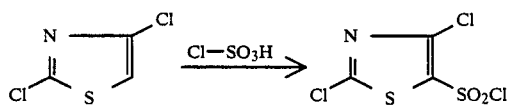

400 g (2.6 mol) of 2,4-dichlorothiazle are introduced in portions in the course of 1.5 hours into 2000 ml (30 mol) of chlorosulphonic acid, with stirring, during which process the temperature rises to approximately 50° C. The mixture was then refluxed for about 7 hours (internal temperature approx 154° C.) After the mixture had cooled, it was discharged dropwise into 10 kg of a stirred ice/water mixture, with external cooling. The precipitate which had formed was then filtered off, washed to neutrality with water and dried at room temperature. Yield: 357 g (54.4 % of the theoretical yield).

The compound can be recrystallized, for example from petroleum ether or from acetonitrile, or can be sublimed at 90° /0.1 mbar. Melting point: 60–61° C.

EXAMPLE 2

Preparation of N-methyl-2,4 dichloro-thiazole-sulphonamide 21 g of a 30% strength aqueous methylamine solution were added dropwise at approx. −75° C. in the course of 45 minute$ to 25.25 g (0.1 mol) Df 2,4-dichlorothiazole-sulphonyl chloride from Example 1 in 250 ml of the cold bath was then removed and the temperature was subsequently allowed to rise to room temperature, the mixture was subsequently stirred for 30 minutes, the resulting suspension was evaporated under a waterpump vacuum, and the residue was stirred with 300 ml of water. The solid was filtered off with suction and chromatographed on silica gel (eluent toluene/EtOH 15:1) in order to remove small amounts of starting material and product which is substituted in the 2-position. 22 g of product were obtained (89% of the theoretical yield) m.p.: 72–3° C.

EXAMPLE 3

Preparation of N-isopropyl-2,4-dichlorothiazole-sulphonamide

In analogy to Example 2, the N-isopropyl-2,4-dichlorothiazole-sulphonamide was prepared by reacting 2,4-dichlorothiazole-sulphonyl chloride from Example 1 with 65% strength aqueous isopropylamine solution.

Following recrystallization from petroleum ether-/acetone 6:1, 26.7 g of product were obtained (97% of the theoretical yield), m.p.: 99°–100° C.

Example 4

Preparation of N,N-dimethyl-2,4-dichlorothiazole-sulphonamide

In analogy to Example 2, the N,N-dimethyl-2,4-dichlorothiazole-sulphonamide was prepared by reacting 2,4-dichlorothiazole-sulphonyl chloride from Example 1 with 45% strength dimethylamine solution. Following recrystallization from petroleum ether/acetone 6:1, 21.7 g of product were obtained (83% of the theoretical yield), m.p.: 89°–90° C.

Example 4A

Preparation of N-cyclopropyl-2,4-dichlorothiazole-sulphonamide

In analogy to Example 2, the N-cyclopropyl-2,4dichlorothiazolesulphonamide was prepared by reacting 2,4-dichlorothiazole-sulphonyl chloride from Example 1 with anhydrous cyclopropylamine Following recrystallization from toluene, 24.4 g of product were obtained (89.2 % of the theoretical yield), m.p.: 90°–91° C.

Example 4B

Preparation of N-allyl-2,4-dichlorothiazole-sulphonamide

In analogy to Example 2, the N-allyl-2,4-dichlorothiazole-sulphonamide was prepared by reacting 2,4-dichlorothiazolesulphonyl chloride from Example 1 with anhydrous allylamine. Following recrystallization from petroleum ether/acetone (6:1), 7.6 g of product were obtained (28% of the theoretical yield), m.p.: 80–81° C.

Example 5

Preparation of N-methyl-2-N,N-dimethylamino-4-chlorothiazole-sulphonamide 33.2 g of a 45% strength aqueous dimethylamine solution were added dropwise in the course of approx. 20 minutes to 24.7 g (0.1 mol) of N-methyl-2,4-dichlorothiazole-sulphonamide from Example 2 in 250 ml of THF, while cooling in an ice bath. The mixture was then allowed to warm to room temperature, subsequently stirred for 30 minutes and evaporated under a waterpump vacuum, and the residue was stirred with 250 ml of water. The solid was filtered off with suction, dried and recrystallized from toluene. 23 g (90%) of colourless crystals were obtained, m.p.: 139° C.

Example 6

Preparation of N-methyl-2-N-phenylamino-4-chlorothiazolesulphonamide

In analogy to Example 5, the N-methyl-2-N-phenylamino-4-chlorothiazole-sulphonamide was prepared by reacting N-methyl-2,4-dichlorothiazole-sulphonamide from Example 2 with aniline. Following chromatography on silica gel using methylene chloride as the eluent, the product having a melting point of 157–8° C. was obtained in 15% yield.

Example 7

Preparation of N-methyl-2-N-isopropylamino-4-chlorothiazole-sulphonamide

In analogy to Example 5, the N-methyl-2-N-isopropylamino-4-chlorothiazole-sulphonamide was prepared by reacting N-methyl-2,4-dichlorothiazole-sulphomamide from Example 2 with a 65% strength aqueous isopropylamine solution. Following recrystallization from toluene, 89% yield of product of m.p. 135° C. were obtained.

Example 8

Preparation of N-isopropyl-2-N,N-dimethylamino-4-chlorothiazole-sulphonamide

In analogy to Example 5, the N-isopropyl-2-N,N-dimethylamino-4-chlorothiazole-sulphonamide was prepared by reacting N-isopropyl-2,4-dichlorothiazole-sulphonamide from Example 3 with 45% strength aqueous dimethylamine solution. Following recrystallization from toluene, the product of m.p. 138° C. was obtained in 74% yield.

Example 9

Preparation of N-isopropyl-2-N-methylamino-4-chlorothiazole-sulphonamide

In analogy to Example 5, the N-isopropyl-2-N-methylamino-4-chlorothiazole-sulphonamide was prepared by reacting N-isopropyl-2,4-dichlorothiazole-sulphonamide from Example 3 with 30% strength aqueous methylamine solution. Following recrystallization from toluene, the product of m.p. 187-8° C. was obtained in a yield of 78% of the theoretical yield.

Example 10

Preparation of N,N-dimethyl-2-N-methylamino-4-chlorothiazole-sulphonamide

In analogy to Example 5, the N,N-dimethyl-2-N-methylamino-4-chlorothiazole-sulphonamide was prepared by reacting N,N-dimethyl-2,4-dichlorothiazole-sulphonamide from Example 4 with 30% aqueous methylamine solution. Following recrystallization from toluene, 88% of the theoretical yield of product of m.p. 194–195° C. were obtained.

Example 11

Preparation of N,N-dimethyl-2-N-isopropylamino-4-chlorothiazole-sulphonamide

In analogy to Example 5, the N,N-dimethyl-2-N-isopropylamino-4-chlorothiazole-sulphonamide was prepared by reacting N,N-dimethyl-2,4-dichlorothiazole-sulphonamide from Example 4 with a 65% strength aqueous isopropylamine solution. An oily product of refractive index $n^{20}_D$ of 1.4563 was obtained in a yield of 92% of the theoretical yield.

Example 12

Preparation of N,N-dimethyl-2-N-phenylamino-4-chlorothiazole-sulphonamide

In analogy to Example 5, the N,N-dimethyl-2-N-phenylamino-4-chlorothiazole-sulphonamide was prepared by reacting N,N-dimethyl-2,4-dichlorothiazole-sulphonamide from Example 4 with aniline. Following recrystallization from methylene chloride, the product of m.p. 162° C. was obtained in a yield of 47% of the theoretical yield.

Example 12A

Preparation of N-cyclopropyl-2-N,N-dimethylamino-4-chloro-thiazole-sulphonamide

In analogy to Example 5, N-cyclopropyl-2-N,N-dimethylamino-4-chlorothiazole-sulphonamide was prepared by reacting N-cyclopropyl-2,4-dichlorothiazolesulphonamide from Example 4A with a 45% aqueous dimethylamine solution. Following recrystallization from toluene, 26.8 g of colourless crystals were obtained (96.5% of the theoretical yield), m.p.: 146°–147° C.

Example 12B

Preparation of N-allyl-2-N,N-dimethylamino-4-chloro-thiazole-sulphonamide

In analogy to Example 5, the N-allyl-2-N,N-dimethylamino-4-chlorothiazolesulphonamide was prepared by reacting N-allyl-2,4-dichlorothiazolesulphonamide from Example 4B with a 45% strength aqueous dimethylamine solution. Following chromatography on silica gel using toluene/ethanol (5:1) as the eluent, 15.7 g of product (56% of the theoretical yield) were obtained.

Example 13

Preparation of N-(3-methoxy-n-propyl)-2-N-(3-methoxy-n-propylamino)-4-chlorothiazole-sulphonamide 40 g of 3-methoxy-n-propylamine were added dropwise at room temperature to a solution of 25.25 g (0 1 mol) of 2,4-dichlorothiazole-sulphonyl chloride from Example 1 in 600 ml of THF, and the mixture was subsequently stirred for 30 minutes at room temperature. After concentrating under a waterpump vacuum, the mixture was stirred with 400 ml of water, the aqueous phase was extracted twice using methylene chloride, and the combined organic phases were dried over magnesium sulphate. After removing the solvent under a waterpump vacuum, 31.3 g of a brown oil were obtained which was chromatographed on silica gel using toluene/ethanol (5:1) as the eluent. 29.3 g (79%) of product were obtained, m.p 55° C.

Example 14

Preparation of N-ethyl-2-N-ethylamino-4-chlorothiazolesulphonamide

In analogy to Example 13, the N-ethyl-2-N-ethylamino-4-chlorothiazole-sulphonamide was prepared by reacting 2,4-di-chlorthiazole-sulphonyl chloride from Example 1 with ethylamine. Following recrystallization from toluene, the product of m.p. 104° C. was obtained in 63% yield.

Example 15

Preparation of N-(2,2-dimethylpropyl)-2-N-(2,2-dimethylpropylamino)-4-chlorothiazole-sulphonamide In analogy to Example 13, the N-(2,2-dimethylpropyl)-2-N-(2, 2-dimethyl-propylamino)-4-chlorothiazolesulphonamide was prepared by reacting 2,4-dichlorothiazolesulphonyl chloride from Example 1 with 2,2-dimethylpropylamine. Following recrystallization from toluene, the product of m.p. 157° C. was obtained in 67% yield.

Example 16

Preparation of N-(2,2,2-trifluoro-1-methylethyl)-2-N(2,2,2-trifluoro-1-methyl-ethylamino)-4-chlorothiazolesulphonamide In analogy to Example 13, N-(2,2,2-trifluoro-1-methyl-ethyl)-2-N-(2,2, 2-trifluoro-1-methyl-ethylamino)-4-chlorothiazole-sulphonamide was prepared by reacting 2,4-dichlorothiazole-sulphonyl chloride from Example 1 with 2,2,2-trifluoro-1-methyl-ethylamine. Following chromatography on silica gel using toluene/ethanol 15:1 as the eluent, the product of m.p. 61° C. was obtained in 13% yield.

Example 17

Preparation of N-methyl-2-N-methylamino-4-chlorothiazolesulphonamide

In analogy to Example 13, the N-methyl-2-N-methylamino-4-chlorothiazole-sulphonamide was prepared by reacting 2,4-dichlorothiazole-sulphonyl chloride from Example 1 with 30% strength aqueous methylamine solution Following recrystallization from diisopropyl ether, the product of m.p 200° C. is obtained in 66% yield.

Example 17A

Preparation of N-cyclopropyl-2-N-cyclopropylamino-4-chlorothiazolesulphonamide In analogy to Example 13, the N-cyclopropyl-2-N-cyclopropylamino-4-chlorothiazolesulphonamide was prepared by reacting 2,4-dichlorothiazole-sulphonyl chloride from Example 1 with cyclopropylamine. Following chromatography on silica gel using toluene/ethanol (5:1) as the eluent, 15.0 g of product were obtained (51% of the theoretical yield), m.p 176°–177° C.

the eluent, were obtained. The product obtained was 30.3 g of colourless crystals (78%), m.p.: 118° C.

Examples 19–26

The monosulphenylated products which are listed in Table 1 were prepared in analogy to Example 18:

TABLE 1

Reaction product

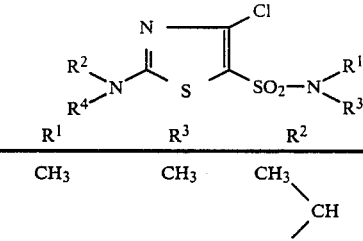

| Example No. | Starting compound from Example No. | R¹ | R³ | R² | R⁴ | M.p. (°C.) | Yield (%) |
|---|---|---|---|---|---|---|---|
| 19 | 11 | $CH_3$ | $CH_3$ | $CH_3$-CH-$CH_3$ | $SCFCl_2$ | 112 | 37 |
| 20 | 12 | $CH_3$ | $CH_3$ | $C_6H_5$ | $SCFCl_2$ | 132 | 48 |
| 21 | 16 | $CF_3$-CH-$CH_3$ | H | $CF_3$-CH-$CH_3$ | $SCFCl_2$ | 54 | 26 |
| 22 | 5 | $CH_3$ | $SCFCl_2$ | $CH_3$ | $CH_3$ | 115 | 91 |
| 23 | 8 | $CH_3$-CH-$CH_3$ | $SCFCl_2$ | $CH_3$ | $CH_3$ | 116 | 32 |
| 24 | 6 | $CH_3$ | $SCFCl_2$ | $C_6H_5$ | H | 152 | 61 |
| 25 | 12A | Cyclopropyl | $SCFCl_2$ | $CH_3$ | $CH_3$ | 122 | 95 |
| 26 | 12B | $CH_2=CH-CH_2$ | $SCFCl_2$ | $CH_3$ | $CH_3$ | 01 | 28 |

Example 18 preparation of N,N-dimethyl-2-(N-dichlorofluorosulphenyl)-methylamino-4-chlorothiazole-sulphonamide A solution of 16.95 g (0.1 mol) of dichlorofluoromethylsulphenyl chloride in 100 ml of $CH_2Cl_2$ was added dropwise, at room temperature and in the course of approx. 20 minutes, to a solution of 25.55 g (0.1 mol) of N,N-dimethyl-2-methylamino-4-chlorothiazole-sulphonamide from Example 10 in 100 ml cf methylene chloride, to which solution 10.5 g of triethylamine had been added The mixture was subsequently stirred for 2 h at room temperature and then washed with two 100 ml portions of water, and the organic phase was dried over magnesium sulphate and concentrated on a rotary evaporator. 36 g of a yellow solid, which was chromatographed over silica gel using methylene chloride as

Example 27

Preparation of N-(N-dichlorofluorosulphenyl-N-methyl)-2-(N-dichlorofluorosulphenyl)-methylamino-4-chlorothiazolesulphonamide 37 3 g (0.22 mol) of dichlorofluoromethylsulphenyl chloride and then 22 22 g (0.22 mol) of triethylamine are added dropwiSe at room temperature to a solution of 24.15 g (0.1 mol) of N-methyl-2-methylamino-4-chlorothiazole-sulphonamide from Example 17 in 300 ml of toluene. The mixture was subsequently stirred for 1 h at room temperature, and then for 1 h at 40° C. 200 ml of water were then added, and the organic phase was dried over $MgSO_4$ and concentrated on a rotary evaporator. After chromatographic filtration of the crude product on silica gel using methylene chloride as the eluent and concentrating the solution, the product was obtained as a pale yellow, viscous oil having a refractive index $n^{20}hd\ D$ of 1.5825. The yield was 40.75 g (51% of the theoretical yield).

Examples 28–34

The disulphenylated products listed in Table 2 were obtained in analogy to Example 27:

TABLE 2

Reaction product $$\begin{array}{c} \text{Cl} \\ \text{N} \underset{R^4}{\overset{R^2}{\diagdown}} \text{N} \overset{}{\underset{S}{\diagup\hspace{-0.5em}\diagdown}} \overset{}{\underset{SO_2-N}{\diagdown}} \overset{R^1}{\underset{R^3}{\diagdown}} \end{array}$$

| Example No. | Starting compound from Example No. | R¹ | R³ | R² | R⁴ | Physical data | Yield (%) |
|---|---|---|---|---|---|---|---|
| 28 | 14 | C₂H₅ | SCFCl₂ | C₂H₅ | SCFCl₂ | $n_D^{20}$: 1.5695 | 78 |
| 29 | 16 | CF₃\CH/CH₃ | SCFCl₂ | CF₃\CH/CH₃ | SCFCl₂ | 01 | 30 |
| 30 | 13 | CH₃O(CH₂)₃ | SCFCl₂ | CH₃O(CH₂)₃ | SCFCl₂ | $n_D^{20}$:1.5509 | 67 |
| 31 | 7 | CH₃ | SCFCl₂ | CH₃\CH/CH₃ | SCFCl₂ | Fp.: 82° C. | 85 |
| 32 | 9 | CH₃\CH/CH₃ | SCFCl₂ | CH₃ | SCFCl₂ | Fp: 91° C. | 77 |
| 33 | 15 | (CH₃)₃C—CH₂ | SCFCl₂ | (CH₃)₃C—CH₂ | SCFCl₂ | Fp.: 118° C. | 88 |
| 34 | 17A | Cyclopropyl | SCFCl₂ | Cyclopropyl | SCFCl₂ | Fp.: 101° C. | 31 |

Use Examples

Example (a)

Venturia test (apple)/protective

Solvent: 4.7 parts by weight of acetone
Emulsifier: 0.3 part by weight of alkylaryl polyglycol ether To produce a suitable preparation of active compound, 1 part by weight of active compound was mixed with the stated amounts of solvent and emulsifier, and the concentrate was diluted with water to the desired concentration, To test for protective activity, young plants were sprayed with the preparation of active compound until dripping wet. After the spray coating has dried on, the plants were inoculated with an aqueous conidia suspension of the apple scab causative organism (Venturia inaequalis) and then remain in an incubation cabin at 20° C. and 100% relative atmospheric humidity for 1 day.

The plants were then placed in a greenhouse at 20° C. and a relative atmospheric humidity of about 70%.

Evaluation was carried out 12 days after the inoculation.

In this test, a clearly superior activity compared with the prior art was shown, for example, by the compounds of the Preparation Examples listed in Table 3

TABLE 3

Venturia test (apple)/protective

| Preparation Example No. | Active compound | Degree of effectiveness as a % of the untreated control at an active compound concentration of 5 ppm |
|---|---|---|
| | according to prior art | |
| | 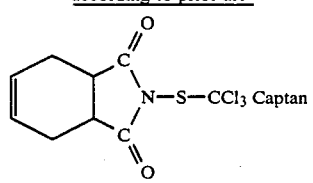 Captan | 63 |
| | according to the invention | |
| 18 | 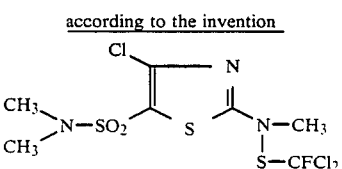 | 89 |

TABLE 3-continued

Venturia test (apple)/protective

| Preparation Example No. | Active compound | Degree of effectiveness as a % of the untreated control at an active compound concentration of 5 ppm |
|---|---|---|
| 19 | $(CH_3)_2N-SO_2-C(Cl)=C(S-)-N=C(S-CFCl_2)-N(CH_3)-CH(CH_3)_2$ | 70 |
| 22 | $CH_3-N(SCFCl_2)-SO_2-C(Cl)=C(S-)-N=C-N(CH_3)_2$ | 82 |
| 23 | $(CH_3)_2CH-N(SCFCl_2)-SO_2-C(Cl)=C(S-)-N=C-N(CH_3)_2$ | 88 |
| 27 | $CH_3-N(SCCl_2F)-SO_2-C(Cl)=C(S-)-N=C(N(CH_3)(SCCl_2F))$ | 86 |

Example (b)

Botrytis test (dwarf bean)/protective

Solvent 4.7 parts by weight of acetone
Emulsifier: 0.3 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating has dried on, 2 small pieces of agar covered with Botrytis cinerea were placed on each leaf The inoculated plants were placed in a darkened humid chamber at 20° C. 3 days after the inoculation, the size of the infected spots on the leaves was evaluated.

In this test, a clearly superior activity compared with the prior art was shown, for example, by the compounds of the Preparation Examples listed in Table 4:

TABLE 4

Botrytis test (dwarf bean)/protective

| Preparation Example No. | Active compound | Degree of effectiveness as a % of the untreated control at an active compound concentration of 100 ppm |
|---|---|---|
| 18 | $(CH_3)_2N-SO_2-C(Cl)=C(S-)-N=C-N(CH_3)(S-CFCl_2)$ | 90 |
| 19 | $(CH_3)_2CH-N(SCFCl_2)-SO_2-C(Cl)=C(S-)-N=C-N(CH_3)_2$ | 95 |

TABLE 4-continued

Botrytis test (dwarf bean)/protective

| Preparation Example No. | Active compound | Degree of effectiveness as a % of the untreated control at an active compound concentration of 100 ppm |
|---|---|---|
| 22 | (structure with Cl, thiazole ring, $CH_3-N(SCFCl_2)-SO_2-$, $-N(CH_3)_2$) | 96 |
| 23 | (structure with Cl, thiazole ring, $Cl_2FCS-N(CH(CH_3)_2)-SO_2-$, $-N(CH_3)_2$) | 82 |
| 27 | (structure with Cl, thiazole ring, $CH_3-N(SCCl_2F)-SO_2-$, $-N(CH_3)(SCCl_2F)$) | 100 |

What is claimed is:

1. 2,4-Dichloro-thiazole-sulphonyl chloride.

* * * * *